US012338147B2

(12) United States Patent
Hendriks et al.

(10) Patent No.: US 12,338,147 B2
(45) Date of Patent: Jun. 24, 2025

(54) DIGESTION OF ORGANIC SLUDGE

(71) Applicant: HASKONINGDHV NEDERLAND B.V., Amersfoort (NL)

(72) Inventors: Antonius Theodorus Wilhelminus Maria Hendriks, Amersfoort (NL); Eddie Koornneef, Amersfoort (NL)

(73) Assignee: HASKONINGDHV NEDERLAND B.V., Amersfoort (NL)

( * ) Notice: Subject to any disclaimer, the term of this patent is extended or adjusted under 35 U.S.C. 154(b) by 765 days.

(21) Appl. No.: 17/437,021

(22) PCT Filed: Feb. 19, 2020

(86) PCT No.: PCT/NL2020/050095
§ 371 (c)(1),
(2) Date: Sep. 7, 2021

(87) PCT Pub. No.: WO2020/180175
PCT Pub. Date: Sep. 10, 2020

(65) Prior Publication Data
US 2022/0177344 A1 Jun. 9, 2022

(30) Foreign Application Priority Data
Mar. 5, 2019 (NL) ...................................... 2022675

(51) Int. Cl.
*C02F 11/04* (2006.01)
*C02F 11/00* (2006.01)
*C02F 11/121* (2019.01)
(52) U.S. Cl.
CPC ............ *C02F 11/04* (2013.01); *C02F 11/004* (2013.01); *C02F 11/121* (2013.01);
(Continued)

(58) Field of Classification Search
CPC .................................................... C02F 11/004
See application file for complete search history.

(56) References Cited

U.S. PATENT DOCUMENTS 4,760,189 A * 7/1988 Mercier ................ C07C 213/02
564/483
5,133,872 A * 7/1992 Baldwin .............. B01D 33/804
210/709

(Continued)

FOREIGN PATENT DOCUMENTS

| GB | 2528110 A | 1/2016 |
| NL | 2021302 B1 | 1/2020 |
| WO | WO-2015037989 A1 * | 3/2015 ............... C02F 3/006 |

OTHER PUBLICATIONS

Novak, JT Drying Technology, 24: 1257-1262, 2006 Copyright # 2006 Taylor & Francis Group, LLC ISSN: 0737-3937 print/1532-2300 online DOI: 10.1080/07373930600840419 (Year: 2006).*

(Continued)

*Primary Examiner* — Magali P Slawski
*Assistant Examiner* — Marriah C G Ellington
(74) *Attorney, Agent, or Firm* — AEON Law, PLLC; Adam L. K. Philipp; Charlotte E. Holoubek

(57) ABSTRACT

The invention is in the field of organic sludge digestion from various sources, such as manure, sludge from a wastewater treatment plant, and an organic fraction of dredging sludge. The present method provides advanced control for serially treating aqueous organic sludge by anaerobic digestion. It further relates to dewatering of the obtained biomass.

20 Claims, 2 Drawing Sheets

(52) U.S. Cl.
CPC .. *C02F 2203/006* (2013.01); *C02F 2209/006* (2013.01); *C02F 2209/02* (2013.01); *C02F 2209/04* (2013.01); *C02F 2209/06* (2013.01); *C02F 2209/10* (2013.01); *C02F 2209/12* (2013.01); *C02F 2209/14* (2013.01); *C02F 2209/20* (2013.01); *C02F 2209/40* (2013.01); *C02F 2209/42* (2013.01); *C02F 2209/44* (2013.01); *C02F 2301/08* (2013.01); *C02F 2303/12* (2013.01)

(56) References Cited

U.S. PATENT DOCUMENTS

| | | | | |
|---|---|---|---|---|
| 2005/0252865 | A1* | 11/2005 | Cerea | C09K 23/54 210/732 |
| 2008/0230484 | A1* | 9/2008 | Burnham | C05F 7/00 210/757 |
| 2012/0125840 | A1 | 5/2012 | Smith | |
| 2013/0022959 | A1* | 1/2013 | Orlewski | C02F 3/286 435/3 |

OTHER PUBLICATIONS

A.A. Tatsi et al. / Chemosphere 53 (2003) 737-744 (Year: 2003).*
Garelli et al , Wat. Sci. Tech. vol. 22, No. 12, pp. 303-308, 1990 (Year: 1990).*
"Chapter 8—Suspended Growth Biological Treatment Processes", Wastewater Engineering: Treatment and Resource Recovery, Metcalf & Eddy, Inc., Published by McGraw-Hill Education, Oct. 16, 2013, pp. 697-751.
International Search Report and Written Opinion, International Application No. PCT/NL2020/050095, mailed May 18, 2020, 10 pages.
"Chapter 13—Processing and Treatment of Sludges", Wastewater Engineering: Treatment and Resource Recovery, Metcalf & Eddy, Inc., Published by McGraw-Hill Education, Oct. 16, 2013, pp. 1502-1535.

* cited by examiner

DIGESTION OF ORGANIC SLUDGE

CROSS-REFERENCE TO RELATED APPLICATIONS

This application is a U.S. national phase entry of and claims priority to PCT International Phase Application No. PCT/NL2020/050095, filed Feb. 9, 2020, which claims priority to NL Patent Application No. NL2022675, filed Mar. 5, 2019. The entire contents of the above-referenced applications and of all priority documents referenced in the Application Data Sheet filed herewith are hereby incorporated by reference for all purposes.

FIELD AND BACKGROUND OF THE INVENTION

The invention is in the field of organic sludge digestion from various sources, such as manure, sludge from a wastewater treatment plant, and an organic fraction of dredging sludge. The present method provides advanced control for serially treating aqueous organic sludge by anaerobic digestion. It further relates to dewatering of the obtained biomass.

For wastewater treatment several stages are typically involved. A primary treatment to remove coarse inorganic material, for instance with screens, to remove sand, for instance with sand traps, and to remove a part of the non-soluble organic material, for instance with primary sedimentation tanks. A secondary treatment may typically be performed using microorganisms that convert biological material being present into sludge. Typically, secondary treatment may include also the removal of pollutants such as phosphates and nitrates and may be combined with a tertiary treatment to further polish the obtained treated wastewater quality. Secondary treatment typically involves an anaerobic zone, an anoxic zone, and an aerobic zone, wherein wastewater is treated with active sludge. The micro-organisms present in the sludge effectuate sludge growth, wherein organic matter is converted into sludge. Surplus sludge may be separated from the treated water by settlement and subsequently discharged from the wastewater treatment plant as waste. Recent improvements however, have managed to breakdown a much larger part of the organic fraction and to use the sludge as a valuable resource. Typically sludge may be thickened and dewatered.

The invention is in the field of anaerobic aqueous sludge reactors and a method of operating such a reactor. Anaerobic reactors are reactors that convert organic material into biogas, with the aid of anaerobic sludge, under anaerobic conditions. The sludge comprises microorganisms.

The term "sludge" is used to refer to a slurry or suspension of inorganic and organic material in an aqueous medium, having a dry solids content between 2 and 12 wt. %, preferably between 3 and 9 wt. %. If sludges are thicker than 12 wt. % it is difficult to digest it in conventional reactors for aqueous sludge flows. Sludge may partially be converted into biogas comprising methane by certain microorganisms. The conversion of sludge into biogas is a complex process and involves many variables and conversion steps, such as hydrolysis, acidogenesis, and methanogenesis, of which hydrolysis is usually a rate-limiting step of the breakdown process.

After anaerobic digestion of the sludge the obtained watery biomass is typically dewatered. It is noted that a dry matter content of the dewatered biomass should be within certain specifications (either legal or practical). The dewatering process itself is also expensive, because of use of poly electrolytes and expensive equipment.

Unfortunately organic sludge digestion from various sources, which sludge may be combined or partly combined in a reactor for digestion, or likewise treated in series, is difficult to optimize, as the composition of the sludge, the microorganisms present, and in general the variables characterizing the sludge varies significantly. The same holds mutatis mutandis for the obtained wastewater. Watery biomass dewatering is done with a dewatering apparatus. For dewatering the variation is even more troublesome since the character of the incoming watery biomass varies also due to the digestion process and this variation is difficult to measure. Typically only dry matter and flux of incoming watery biomass into the dewatering apparatus are measured. Dry matter content is typically inaccurately measured, e.g. because measuring instruments have a tendency for fouling, and also air bubbles in the aqueous effluent disturb the measurement. To overcome this inaccuracy control parameter settings are typically chosen conservatively, involving a higher dosing of polyelectrolytes and a lower applied pressure on the sludge, which is sub-optimal. This approach is however still preferred due to the unknown watery biomass dewatering characteristics; with a same dry matter content and same process parameter settings a different dewatering result may still be obtained. There is no way to predict which dewatering result will be obtained. Moreover the conservative approach is also preferred to adapt to changes such as in watery biomass composition and flux which are found to occur regularly. In general control systems are found to react slowly towards changes.

It is further noted that dewatered biomass is often discarded. In issue with biological matter may be that potentially pathogenic microorganisms may (still) be present after treatment. Therefore the biomass can often not be used further, such as soil improver, and could need further treatment in order to reduce the risk of the pathogenic microorganisms. Typically high temperatures and/or long residence times are used to obtain sufficient reduction of pathogenic microorganisms. In this respect reference is made to EPA503 relating to biosolids of class A.

In general measuring or monitoring concentrations and other parameters during wastewater treatment is well established in the art, though not always very accurate. These parameters are measured via widely available instrumentation in wastewater treatment processes. Using such instruments to control biological treatment systems, and in particular to control the aeration input to a treatment system is well established.

A general reference for digestion of wastewater treatment is Eddy, M. A., Burton, F. L., Tchobanoglous, G. and Tsuchihashi, R., 2013. Wastewater engineering: treatment and Resource recovery (p. 2048). McGraw-Hill Education: New York, NY, USA. which reference and its contents are incorporated by reference.

Further reference can be made to WO2015/037989 A1 (see below), US 2012/125840 A, and GB 2 528 110 A. US 2012/125840 A recites systems and methods for performing anaerobic digestion of biomaterials using a clarifier, a batch reactor, and/or a digester are disclosed. GB 2 528 110 A recites a mobile anaerobic digestion plant for the high-rate anaerobic digestion of organic waste comprises a reactor system, a control system, and a heating system, mounted on or in a vehicle or towable trailer. The reactor system includes two or more reactor tanks, operable in series or in parallel, with a gas collection system in at least one reactor tank. The systems and methods therein are not suited for pathogenic control, and certainly not in combination with control of digestion under conditions leading to at least acceptable results.

The present invention therefore relates to an improved method for serially treating aqueous organic sludge by anaerobic digestion, which overcome one or more of the above disadvantages, without jeopardizing functionality and advantages.

SUMMARY OF THE INVENTION

The present invention relates in a first aspect to a method of serially treating aqueous organic sludge by anaerobic digestion, comprising (a1) partly or fully feeding input sludge to a first digestion reactor in a series of N digestion reactors and feeding a controlled part of 0-50% of the input sludge (directly) to a second digestion reactor, wherein N≥2, such as N≥5, (a2) feeding an effluent of an nth digestion reactor through a fluidic connection to an n+1th digestion reactor, wherein n∈[1,N], (a3) feeding a controlled part of 0-70% of the effluent of the Nth (last) digestion reactor through a fluidic connection to at least one lower ranked (n∈[1,N−1]) digestion reactor, (a4) feeding a controlled part of 0-50% of an effluent of the second digestion reactor through a fluidic connection to the first digestion reactor, (a5) removing a controlled part of 30-100% (a remainder) of the effluent of the Nth (last) digestion reactor to a fluidic connection, such as to a post-digestion reactor and/or to a dewatering apparatus, (b) controlling at least one feeding or removing (a1-a5) by (b1) obtaining at least two values (a first and second value thereby establishing a potential variation or change in said value) of (b11) pH, (b12) an amount of dry sludge in the feed, (b13) temperature of at least one digestion reactor, (b14) type of input sludge, and optionally at least one of (b30) concentration of fatty acids and (b37) alkalinity, which may be obtained separately or in combination, such as with one measurement device, and optionally obtaining (b35) redox values, wherein values are obtained of at least one of the sludge in the input and of at least the first of the N digestion reactors, and by (b2) regulating (b2b) a fluid level in a digestion reactor, and a parameter selected from (b2a) at least one flow, (b2c) an amount of sludge in a digestion reactor, (b2d) an amount of anti-foam in a digestion reactor, and combinations thereof, wherein a flow (b2a) is selected from flows (a1-a5), (c) optionally digesting the organic sludge, during a period of time of more than 3 days, in at least one digestion reactor, at a temperature from 20-70° C. and optionally (d) feeding the sludge from the Nth digestion reactor to a post-digesting reactor (11), preferably after the Nth digestion reactor, and/or (e) dewatering the formed biomass, and controlling dewatering by (b1) obtaining characteristics of the sludge in the input and of at least the first of the N digestion reactors and by regulating (b3) a flow between at least one Nth digestion reactor and dewatering apparatus. The present digestion may be operated under mesophilic conditions (20-45° C.) and/or thermophilic conditions (45-70° C.), wherein thermophilic conditions provide the advantage of reducing a number of pathogenic microorganisms significantly. With the present method and device control and regulation is significantly improved resulting in more than sufficient reduction of pathogenic organisms as well as in good yields and proper digestion. This is achieved under relatively mild temperature conditions, with relatively short retention times. In fact, a two-reactor system is for certain applications already sufficient for this purpose. For instance foam formation is minimized (hardly or no foam) and digestion is optimized (from about 30% to about 80% of dry matter digested). It is noted that abundant foam formation implies that a reactor may need to be shut down and restarted, or at least digestion is interrupted. The present applicant has filed WO 2015/037989 A1 and NL 2021302, which documents and their contents are incorporated by reference. They provide amongst others certain details of reactor setups, operation conditions, and of dewatering. As mentioned above the input sludge may come from a largely variety of sources and from different sources. The input sludge is at least partly provided to a first digestion reactor, or likewise first digestion, and optionally partly to a second digestion reactor, e.g. depending on status of the digestion reactors, dewatering apparatus, and incoming sludge characteristics. The output (effluent) of a digestion reactor is fed to a subsequent digestion reactor. Part of the effluent of the second digestion reactor may be fed back to the first digestion reactor. Likewise part of the effluent of the last digestion reactor may be fed back to a previous digestion reactor, such as first or second digestion reactors. It is noted that controlling (b2b) a fluid level in a digestion reactor typically relates to limiting or preventing overflow of an nth reactor to a subsequent n+1th reactor, thereby preventing contamination of the n+1th reactor such that pathogenic organisms are sufficiently reduced in number, typically at least by a factor 1000. Overflow can further, or in addition, be prevented by at least partly emptying an nth reactor, and thereafter at least partly emptying an n−1th reactor, typically starting with the last (Nth) reactor. The control of this part of the process, and likewise of the dewatering, is done by obtaining certain parameters, such as pH, redox values, and regulating flows between subsequent and/or feedback digestion reactors, such as by using valves. These parameters are obtained from digestion reactors, from input sludge, from feedback sludge, and from dewatering input and dewatering output. Before dewatering the organic sludge is digested, at a temperature from 20-70° C. during a period of time of more than 3 days, such that a majority of the organic material is digested and that a number of pathogenic microorganisms is reduced significantly and is preferably zero. As mentioned, in a further step the digested biomass is dewatered. The invention therefore provides a control system that can substantially improves treatment of a variety of input biomasses, reduces costs, improves a quality of a final product obtained, reduces use of chemicals, reduces labor, and increases an amount of biogas produced.

The present invention provides good control. Also it is possible to obtain biosolids Class A material. It is found that already in the second reactor biosolids Class A material can be obtained. Even further, such as when using the Ephyra® technology, higher throughputs can be achieved.

In a second aspect the present invention relates to a reactor set-up for serially treating aqueous organic sludge by anaerobic digestion, comprising a series of N digestion reactors (1,N), wherein N≥2, between an nth digestion reactor and an n+1th digestion reactor a fluidic connection, a sludge input for the first digestion reactor, an effluent output for the Nth digestion reactor, a post-digesting reactor 11 in fluid connection with the Nth digestion reactor, an optional dewatering device 21 in fluid connection with the post-digesting reactor, a fluidic effluent connection between the second digestion reactor and the first digestion reactor, a fluidic effluent connection between the Nth digestion reactor and at least one lower ranked (n∈[1,N−1]) digestion reactor, an effluent output for the Nth digestion reactor, at least one controller for controlling at least one feeding or removing (a1-a5) by (b1) obtaining at least two values of (b11) pH, (b12) an amount of dry sludge in the feed, (b13) temperature of at least one digestion reactor, and (b14) type of input sludge, and (b37) alkalinity, and optionally obtaining (b35) redox values, wherein values are obtained of at least one of the sludge in the input and of at least the first of the N digestion reactors, and by (b2) regulating (b2b) a fluid level in a digestion reactor, and a parameter selected from (b2a) at least one flow, (b2c) an amount of sludge in a digestion reactor, (b2d) an amount of anti-foam in a digestion reactor, and combinations thereof, wherein a flow (b2a) is selected from flows (a1-a5), and for controlling dewatering by (b1) obtaining values of (b11) pH and (b35) redox values, wherein values are obtained of at least one of the sludge in the input and of at least the first of the N digestion reactors and by regulating (b3) a flow between at least one Nth digestion reactor and/or optional post-digesting reactor and dewatering apparatus, at least one heater for digesting the organic sludge during a period of time of more than 3 days in at least one digestion reactor at a temperature from 20-70° C., and at least one pump for providing flow.

Thereby the present invention provides a solution to one or more of the above-mentioned problems.

Advantages of the present invention are detailed throughout the description.

DETAILED DESCRIPTION OF THE INVENTION

The present invention relates in a first aspect to a method according to claim 1.

In an exemplary embodiment the present method may further comprise (d) feeding the sludge from the Nth digestion reactor to a post-digesting reactor 11, preferably after the Nth digestion reactor.

In an exemplary embodiment the present method may further comprise (e) feeding a dewatering apparatus 21 from the Nth digestion reactor and/or post-digester, dewatering the formed biomass, and controlling dewatering by (b1) obtaining characteristics of the sludge in the input and of at least the first of the N digestion reactors and by regulating (b3) a flow between at least one Nth digestion reactor and/or post-digesting reactor and dewatering apparatus.

In an exemplary embodiment of the present method one or more buffers are provided before the dewatering apparatus.

In an exemplary embodiment of the present method controlling feeding and/or controlling dewatering may further comprise obtaining at least one of (b15) feed flux, (b16) production installation of input sludge, (b17) method of production of input sludge, (b18) age of input sludge, (b19) organic carbon content (COD) of input sludge, (b20) method of production of input sludge, (b21) dosing of chemicals during production of input sludge, (b22) remaining concentration of dosing chemicals left, (b23) process setting during production of input sludge, (b24) polyelectrolyte concentration, (b25) type of polyelectrolyte, (b26) bowl speed, (b27) pressure applied to the sludge, (b28) gas produced, (b29) ammonium concentration in an effluent stream, preferably the effluent stream of the Nth digestion reactor, (b30) concentration of fatty acids, (b31) concentration of proteins, (b32) concentration of sugars, (b33) concentration of cellulosic material, (b34) amount of degradable organic matter, (b35) boundary conditions during production of the input sludge, (b36) volatile fatty acid concentration, (b37) alkalinity, such as bicarbonate concentration, (b38) cation concentration, such as Na, Ca, and Mg concentration, e.g. in order to prevent or limit phosphate minerals, such as struvite, from depositing in the digestion reactor, (b39) differential speed, and (b40) trace elements, such as by feeding back effluent from a higher ranked reactor to a lower ranked reactor, e.g. last to first reactor. Many variables may be taken into account. Some of these variables are found to be relatively important in most cases, whereas other may be important only in some cases. However, based on these variables (also including pH and redox values) an obtaining data with respect to these variables, a much better control of the digestion, and later on also of post-digestion and dewatering, is obtained. The variables are typically used to adjust settings of the reactors and apparatuses. These adjustment can typically be made in view of previously performed digestions, with comparable input feeds of sludge. As such the present method reaches optimal conditions much faster, reducing consumption of materials and chemicals and energy, reducing waste, and improving biogas yield.

In an exemplary embodiment of the present method N is from 2-10, preferably 3-8, more preferably 3-6, such as 3-5, such as 4. Hence the number of reactors, or likewise compartments, is typically not too high.

In an exemplary embodiment the present method may comprise feeding a controlled part of 0-50% of the input sludge to a second digestion reactor, preferably 0.1-10% of the input sludge, more preferably 0.5-5% of the input sludge, even more preferably 3-5% of the input sludge. In certain cases the first digestion reactor may not be circumvented, such as in view of government regulations, and then nothing of the input feed is passed to the second digestion reactor.

In an exemplary embodiment the present method may comprise feeding a controlled part of 0-50% of an effluent of the second digestion reactor through a fluidic connection to the first digestion reactor, preferably 0.5-20% of the effluent of the second digestion reactor, more preferably 1-10% of the effluent of the second digestion reactor, such as 1.5-5%, of the effluent of the second digestion reactor.

In an exemplary embodiment the present method may comprise phased feeding a controlled part of 0-50% of the effluent of the first digestion reactor through a fluidic connection to at least a second digestion reactor when the effluent feedback of the Nth digestion reactor to the first digestion reactor has reached a predetermined set-point, preferably 1-30% of the effluent of the first digestion reactor, more preferably 2-10% of the effluent of the first digestion reactor, wherein the predetermined setpoint is 20% of the effluent of the Nth digestion reactor, preferably 10% of the effluent of the Nth digestion reactor, preferably in combination with keeping the pH above 5.0, preferably above 5.2, such as above 5.6, for at least the first digestion reactor, and preferably for most or all of the digestion reactors. Likewise a part of the effluent of the first reactor may be provided to the post-digester.

In an exemplary embodiment the present method may comprise feeding a controlled part of 0-50% of the effluent of the Nth digestion reactor through a fluidic connection to at least a first digestion reactor, preferably 1-30% of the effluent of the Nth digestion reactor, more preferably 2-10% of the effluent of the Nth (last) digestion reactor.

In an exemplary embodiment the present method may comprise feeding a controlled part of 0-30% of the effluent of the Nth digestion reactor through a fluidic connection to at least a second digestion reactor, preferably 1-10% of the effluent of the Nth digestion reactor, more preferably 2-5% of the effluent of the Nth digestion reactor.

In an exemplary embodiment the present method may comprise feeding a controlled part of 50-100% of the effluent of the Nth digestion reactor through a fluidic connection to a dewatering apparatus and/or to a post digester, preferably 60-98% of the effluent of the Nth digestion reactor, more preferably 80-90% of the effluent of the Nth digestion reactor.

With the above controls amongst others the digestion of the various reactors is optimized, for instance in terms of pH and/or redox potential.

In an exemplary embodiment of the present method digesting the organic sludge is in at least two digestion reactors, preferably in 2 to N digestion reactors, more preferably in 3 to 5 digestion reactors.

In an exemplary embodiment of the present method thermophilic digestion is in each digestion reactor independently at a temperature from 50-65° C., preferably from 52-60° C., more preferably from 53-58° C., such as from 55-57° C. Digestion at higher temperature is found to reduce pathogenic microorganisms significantly. As such biosolids Class A may be obtained. In an alternative, or in addition mesophilic digestion is in each digestion reactor independently at a temperature from 25-40° C., preferably from 30-38° C., such as from 35-37° C. Less energy is then used.

In the present method a total solid retention time (SRT) for digestion is a period of time of 3-30 days, preferably 4-21 days, more preferably 5-18 days, such as 6-15 days, e.g. 8-12 days.

In an exemplary embodiment of the present method the digestion period is a combined period of at least one digestion reactor.

In an exemplary embodiment of the present method digesting is in at least one of $n \in [1-N]$ continuous stirred tank reactors, $n \in [1-N]$ batch reactors, a single reactor with $n \in [1-N]$ segmented sub-reactors, such as vertically separated compartments, and $n \in [1-N]$ plug flow reactors, preferably $n \in [1-N]$ plug flow reactors. In this respect a fluid connection may relate to a tube-like structure, or simply to a partial absence of an intermittent wall. An issue which may occur is a decrease (acidification) of a reactor, and in particular of the first digestion reactor. By feeding an effluent of an Nth digestion back to the first digestion reactor, and likewise of the second digestion reactor, pH may be controlled.

In an exemplary embodiment of the present method flow between reactors, and towards a dewatering apparatus, is controlled.

In an exemplary embodiment of the present method input sludge is one or more of manure, primary and secondary sludge from treated wastewater, and dredging.

In an exemplary embodiment of the present method input sludge and or a digestion reactor comprises at least two different sludges, such as 3-10 different sludges, such as primary or secondary sludge, "winter" or "summer" sludge, sludge from a different wastewater plant, etc. Sludge may also be different in terms of characteristics.

In an exemplary embodiment of the present method dewatering is performed in at least one of a belt filter press, a centrifuge, a dewatering screw, a drum thickener, a filter press, and a gravity belt.

In an exemplary embodiment of the present method controlling further comprises comparing obtained data and/or predicted data from the sludge with stored data, preferably stored data on a computer, on a server, or in the cloud,
  identifying a set in the stored data which is similar to the obtained/predicted data,
  retrieving method operational settings related to the set of stored data for operating at least digestion reactor and/or a dewatering device, and
  applying at least one of the retrieved operation settings to at least digestion reactor and/or dewatering device.

In an exemplary embodiment of the present method controlling comprises adapting at least one of pH, redox potential, volatile fatty acid concentration, alkalinity, cation concentration, and temperature, of at least one digestion reactor and/or dewatering device, such as by adapting at least one flow (a1)(a5).

In an exemplary embodiment of the present method obtained data is mathematically weighed.

In an exemplary embodiment of the present method obtained data is mathematically averaged.

In an exemplary embodiment of the present method to be obtained data is mathematically predicted.

With the above weighing, averaging, and predicting, the performance of the digestion can be controlled on a statistical basis; deviations can be identified quickly, and process conditions may then be adapted; also process conditions of subsequent reactors and apparatuses may be adapted quickly, and at a required time. In addition no reaction needs to be taken if process conditions remain within process such as production limits.

In an exemplary embodiment of the present method the method is performed continuously.

In an exemplary embodiment of the present method the method is performed at regular intervals, such as every 1-60 minutes.

In an exemplary embodiment of the present method the method is performed after an incident. As specially in such cases a restart or reboot of the method and system may be required.

In an exemplary embodiment of the present method the method is performed based on statistical process control, and combinations of the above. An example is e.g. given in the above NL 2021302 application.

In an exemplary embodiment of the present method dry matter is measured, such as with a turbidity measurement device, preferably a turbidity measurement device in parallel to a fluid connection, with a radio wave device, with an optical device, or a combination thereof.

In an exemplary embodiment of the present method flow is controlled with at least one valve, at least one pump, and combinations thereof.

In an exemplary embodiment of the present method during dewatering a dry matter content is measured every 0.1-2440 minutes, preferably every 1-15 minutes, such as every 2-7 minutes.

In an exemplary embodiment of the present method a dry matter content is used to adapt setting of the dewatering device.

In an exemplary embodiment of the present method the pH of at least one digestion reactor is controlled to maintain above 5.5, preferably above 5.8, typically for at least the first digestion reactor, and preferably for each digestion reactor.

In an exemplary embodiment of the present method the redox value of at least one digestion reactor is controlled to maintain below −200 mV, preferably below −300 mV, typically for at least the first digestion reactor, and preferably of each digestion reactor.

In an exemplary embodiment of the present method the pH of at least one digestion reactor is controlled to maintain below 9, preferably below 8, typically for at least the first digestion reactor, and preferably of each digestion reactor.

In an exemplary embodiment of the present method the redox value of at least one digestion reactor is controlled to maintain above −450 mV, typically for at least the first digestion reactor, and preferably of each digestion reactor.

In an exemplary embodiment of the present method an amount of foam is controlled by adding 0.01-1 wt. % anti-foam, preferably 0.02-0.2 wt. %, such as 0.05-0.1 wt. %

In an exemplary embodiment of the present method antifoam comprises a component selected from essential oils, fatty acid esters, poly alkyl glycols, alkane hydrocarbons, poly dimethyl siloxane, silicon emulsions, polyethers, sili-con polymers, Simethicone, derivatives thereof, and combinations thereof. Examples of suitable antifoams are Struktol J 673-1 A, Struktol SB 2080, and Struktol SB 2322 of Struktol, DeFoam 3000 of TeamAquaFix, Silicone anti-foaming emulsion of CarlRoth, and Antifoam 204, Silicone antifoam, Antifoam B emulsion, Antifoam A concentrate, Antifoam Y-30 Emulsion, Antifoam SE-15, EX-CELL antifoam and Simethicone of Sigma-Aldrich.

In an exemplary embodiment of the present method an effluent of the Nth reactor is treated in a stirred tank reactor before dewatering.

In an exemplary embodiment of the present method microbial sludge is granulated, is flocculate, forms a biofilm, or a combination thereof.

In an exemplary embodiment of the present method the system is loaded with >1 kg COD, preferably >2 kg, more preferably >5 kg, such as up to 20 kg, per m3 system volume/day. Typically 6-8 kg is used.

In an exemplary embodiment of the present method at least one flow is monitored by a power consumption of a pump providing said flow.

In an exemplary embodiment of the present method aqueous sludge is pre-treated prior to step (a), preferably by at least one of clarification, grit removal, fat removal, grease removal, pH-adjustment, and pre-sedimentation, and/or
wherein >2 kg sludge/m3 is present per reactor, preferably >2.5 kg sludge/m3, such as 5-80 kg sludge/m3. In terms of dry solids the amounts are up to 80 kg DS/m3 per reactor, per day, such as 27 kg DS/m3, especially in the first reactor/compartment.

The invention is further detailed by the accompanying figure and example, which are exemplary and explanatory of nature and are not limiting the scope of the invention. To the person skilled in the art it may be clear that many variants, being obvious or not, may be conceivable falling within the scope of protection, defined by the present claims.

DESCRIPTION OF THE SEVERAL VIEWS OF THE INVENTION

Figure 1:
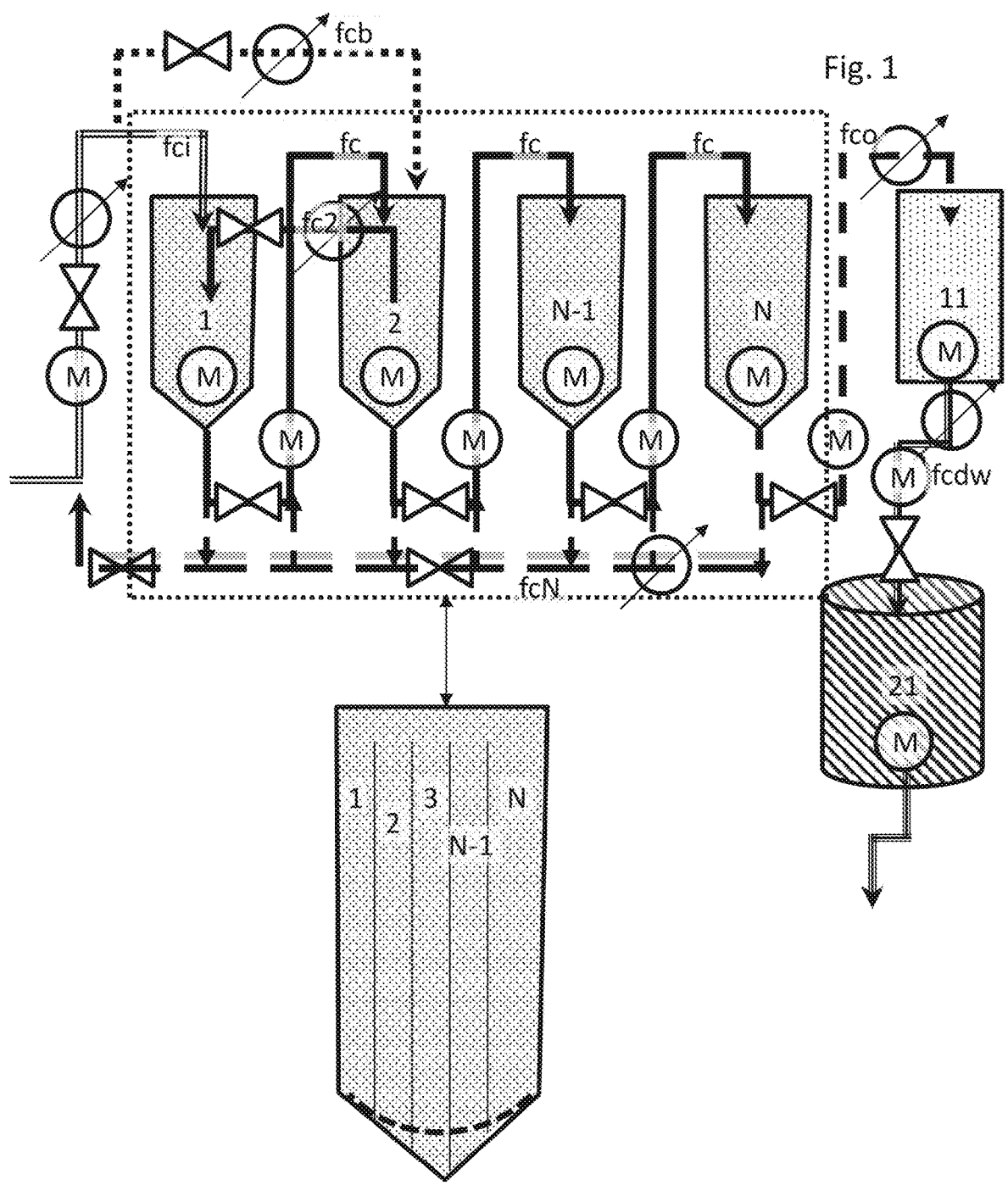
FIG. 1-3 show details of the invention.

FIG. 1 shows schematics of a reactor set-up. 1–N reactors in series are shown, which may also relate to a reactor having 1–N compartments (lower part of the figure). This single reactor may have a curved or flat bottom, represented by the dashed line, being an alternative to the narrowing bottom. The M indicates measurements that can take place. A post-digester 11 and dewatering unit 21 are further shown. Part of the input can be directly fed to reactor 2 (dotted upper line). Part of the output of the last (Nth) reactor can be fed to a lower ranked reactor (lower dashed line). Also parts of higher ranked reactors may be fed to lower ranked reactors. This may be through a common line, or to at least one further, additional line, represented by the grayish line. Part of the second reactor can be fed back to the first reactor (solid line).

Figure 2:
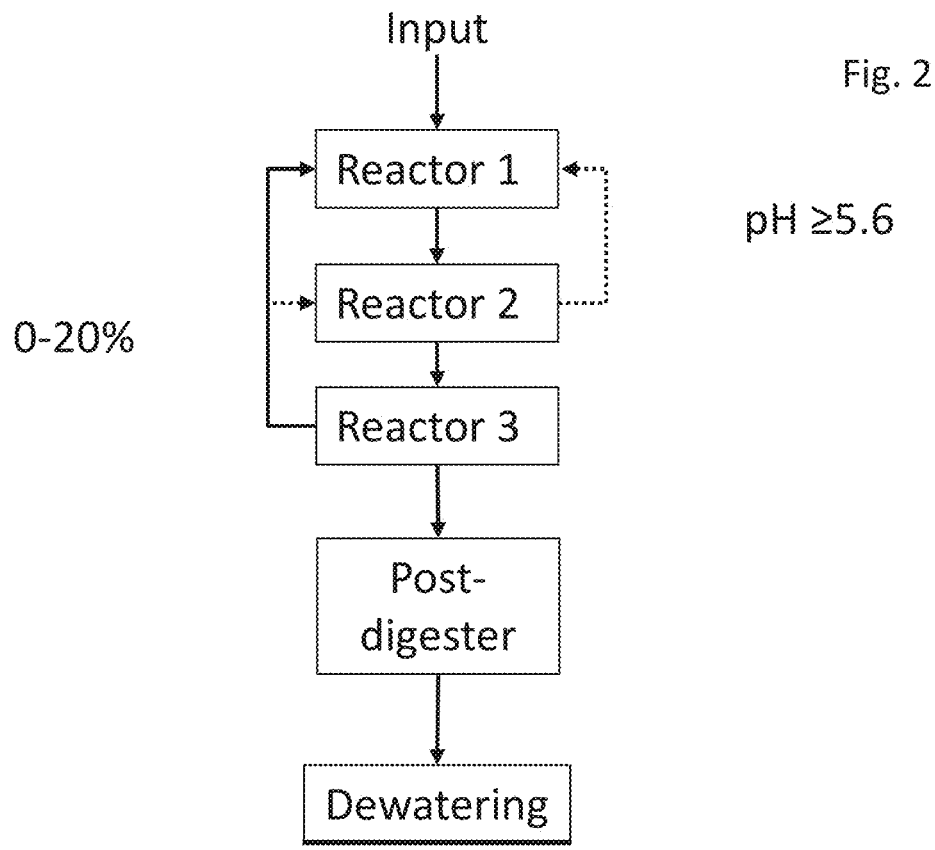

FIG. 2 shows schematics of the method of operation. Part of the contents of reactor 3 are fed back to reactor 1, and part of the contents of reactor 3 are fed back to reactors 1 and 2 respectively, typically 0-20% thereof. The pH is maintained at above 5.6. The output of reactor 3 is fed to a post-digester. The output thereof can be further treated, e.g. dewatered.

Figure 3:
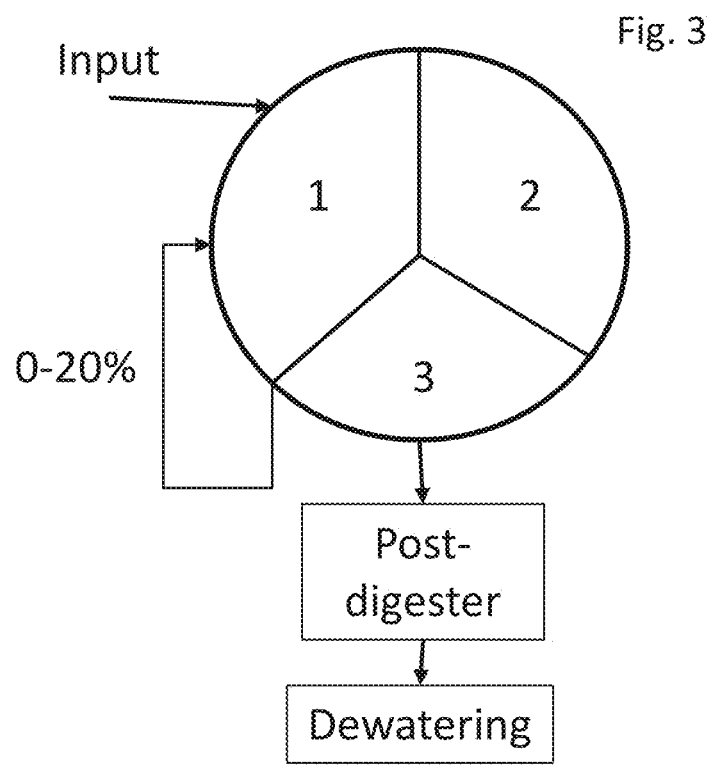

FIG. 3 shows schematically that part of the input is recirculated, part is post-digested, and part remains in the series of reactors for a given time.

The figures are further detailed in the description and examples below.

EXAMPLES/EXPERIMENTS

The below relates to an example of the present invention.

In the present invention use is made of the Ephyra® technology, which is typically applied for mesophilic processes. In this plug flow process the residence time is almost the same for all solids. This is more efficient compared to a conventional digester based on a continuous stirred tank reactor (CSTR), where a fraction of the solids has a lower residence time than the average residence time. The Ephyra® technology uses multiple compartments for digestion, therefore phase separation can take place. The phase separation causes to have mainly fatty acid production in the first compartment, therefore decreasing the pH significant in the first compartment. A recirculation flow from the last compartment is used to control the pH in the first compartment and (re)inoculation of the first compartment. There is a limit on the recirculation rate since a high recirculation rate causes the process to become more like a conventional CSTR digester. The Ephyra® concept caused an extra up to 25% of organic waste degradation, up to 25% enhanced biogas production and the capability to maintain higher loading rates, which decrease needed reactor volume. The technology also caused a better dewaterability, in turn decreasing the amount for sludge transportation. To meet demands for biosolids Class A qualification the sludge should at least comply with one of the following pathogen reduction requirements: fecal coliforms<1,000 Most Probable Number (MPN)/g Total Solids (TS) or Salmonella species<3 MPN/4 grams of TS. Next to pathogen reduction, the sludge's Volatile Solids (VS) concentration needs to be decreased with at least 38%.

Three reactors in series were used. The reactors each had a volume of 21.5 l, and were kept at 55° C. The pH was maintained in a range of 5.6-7.6 for each reactor. The first reactor typically had a lower pH than the second reactor, and the second reactor had a lower pH than the third reactor. The RT per reactor was 4 days, thus a total RT of 12 days. In practice not much difference between solid retention time and hydraulic retention time was found, if any. As starting material recirculation sludge from a thermophilic digester of a wastewater treatment plant (WWTP) in Zwolle was used. The reactors were fed with a mixture of 40% primary sludge, 60% secondary sludge, having 4 wt. % DS and 3 wt. % ODS from a WWTP in Amersfoort. Before usage the sludge was filtered with a sieve to remove large particle that could cause clogging of the tubes. The temperature, pH, DS and ODS were controlled. During the project 5 peristaltic pumps were used: 1 for the influent, 1 for the effluent, 1 for the recirculation and 1 between the first and second reactor and 1 between the second and third reactor. The pumps were set with a timer to pump 5-10 minutes every hour. The pumps were calibrated with water first, afterwards sludge was used to ensure the set point flow. To avoid acidification in the first reactor the recirculation flow was 10%. The first weeks were for starting up the reactor during which the following parameters were measured: temperature; pH; TS content; VS content. The temperature and pH were measured with corresponding sensors. The TS content was determined by drying samples in an oven at 105° C. The Volatile Solids (VS) concentration of the sludge was measured by incineration in an oven at 550° C. The temperature and pH were measured multiple times every working day. The influent's TS and VS content was measured after new sludge is retrieved from the WWTP in Amersfoort, while the effluent's TS and VS content of each reactor were measured every other working day. The TS and volatile solids (VS) were determined using crucibles and an 'Denver Instrument Company AA-250' analytical balance according to Standard Methods. A 'Memmert ULM500' oven and 'EUROTHERM 808' muffler furnace was used for drying and burning respectively. A "Hach HQ40D" meter was used for pH measurements. The temperature was measured with a "Voltcraft PL-125-T2". A thermocouple was attached to the outside of each reactor and insulated with PU-foam.

The TS in reactor 3 was some 2.8 wt. %, in reactor 2 some 3.0 wt. % and in reactor 1 some 3.5 wt. %. The VS in reactor 3 was some 1.7 wt. %, in reactor 2 some 2.0 wt. % and in reactor 1 some 2.5 wt. %. Variations over time did occur.

Therein a pathogenic reduction was obtained. Coliforms were <1000 colony forming units (Mots Probable Number: MPN)/g dry matter (DS) in the effluent, salmonellas were likewise <3 MPN/g DS, and ODS digestion was >38%. The ODS reduction was best in the third reactor (some 40%), some 30% in the second reactor, and some 20% in the first reactor.

Depending of the residence time in the reactors the digestate cake had a dry solid content of >16.5 wt %.

In conclusion biosolids Class A biological matter is produced.

The invention claimed is:

1. A method for serially treating aqueous organic sludge by anaerobic digestion, comprising
   (a1) feeding input sludge through a fluidic connection to a first digestion reactor in a series of N digestion reactors and feeding a controlled part of the input sludge through a fluidic connection to a second digestion reactor, wherein N≥2,
   (a2) feeding an effluent of an nth digestion reactor through a fluidic connection to an n+1th digestion reactor, wherein n is an element of [1,N],
   (a3) feeding a controlled part of the effluent of the Nth digestion reactor through a fluidic connection to at least one lower ranked digestion reactor,
   (a4) feeding a controlled part of an effluent of the second digestion reactor through a fluidic connection to the first digestion reactor,
   (a5) removing a controlled part of 30-100% of the effluent of the Nth digestion reactor from the series of N digestion reactors,
   (b) controlling at least one of the group of feeding and removing
      by (b1) obtaining concentration of fatty acids, and at least two values of (b11) pH, an amount of dry sludge in the feed, temperature of at least one digestion reactor, and type of input sludge, and
      by (b2) regulating a fluid level in at least one digestion reactor to prevent overflow of an nth reactor to a subsequent n+1th reactor and by regulating a fluid level by at least one parameter selected from at least one flow, an amount of sludge in a digestion reactor, and an amount of anti-foam in a digestion reactor, wherein a flow is selected from flows a1-a5, and
   (c) digesting the organic sludge, during a period of time of more than 3 days, wherein a total solid retention time for digestion is a period of time of 3-21 days, in at least one of the series of N digestion reactors, at a temperature from 20-70° C.

2. The method according to claim 1, further comprising
   (d) feeding the sludge from the Nth digestion reactor to a post-digester.

3. The method according to claim 1, comprising
   (e) feeding a dewatering apparatus from the Nth digestion reactor and post-digester, dewatering the formed biomass, and controlling dewatering by obtaining characteristics of the sludge in the input and of at least the first of the N digestion reactors and by regulating a flow between at least one Nth digestion reactor and post-digester and dewatering apparatus.

4. The method according to claim 3, wherein one buffer is provided before the dewatering apparatus.

5. The method according to claim 1, wherein controlling feeding and controlling dewatering further comprises obtaining at least one of feed flux, production installation of input sludge, method of production of input sludge, age of input sludge, organic carbon content of input sludge, method of production of input sludge, dosing of chemicals during production of input sludge, remaining concentration of dosing chemicals left, process setting during production of input sludge, polyelectrolyte concentration, type of polyelectrolyte, bowl speed, pressure applied to the sludge, gas produced, ammonium concentration in an effluent stream, concentration of proteins, concentration of sugars, concentration of cellulosic material, amount of degradable organic matter, boundary conditions during production of the input sludge, volatile fatty acid concentration, cation concentration, differential speed, and trace elements.

6. The method according to claim 1, wherein N is from 2-10.

7. The method according to claim 1, comprising
   feeding a controlled part of 0-50% of the input sludge to a second digestion reactor, and
   feeding a controlled part of 0-50% of an effluent of the second digestion reactor through a fluidic connection to the first digestion reactor, and
   phased feeding a controlled part of 0-50% of the effluent of the first digestion reactor through a fluidic connection to at least a second digestion reactor when the effluent feedback of the Nth digestion reactor to the first digestion reactor has reached a predetermined setpoint, and
   feeding a controlled part of 0-70% of the effluent of the Nth digestion reactor through a fluidic connection to at least one lower ranked digestion reactor, and
   feeding a controlled part of 0-30% of the effluent of the Nth digestion reactor through a fluidic connection to at least a second digestion reactor, and
   feeding a controlled part of 50-100% of the effluent of the Nth digestion reactor through a fluidic connection to a dewatering apparatus and to a post-digester.

8. The method according to claim 1,
   wherein digesting the organic sludge is in at least two digestion reactors, and
   wherein digestion is in each digestion reactor independently at a temperature from 50-65° C., and wherein a total solid retention time for digestion is a period of time of 4-21 days, and wherein the digestion period is a combined period of at least one digestion reactor.

9. The method according to claim 1, wherein digesting is in at least one of n is an element of [1,N] continuous stirred tank reactors, n is an element of [1,N] batch reactors, a single reactor with n is an element of [1,N] segmented sub-reactors, and n is an element of [1,N] plug flow reactors.

10. The method according to claim 1, wherein input sludge is one of manure, primary and secondary sludge from treated wastewater, and dredging; and wherein at least one selected from input sludge and a digestion reactor, comprises at least two different sludges.

11. The method according to claim 1, wherein dewatering is performed in at least one of a belt filter press, a centrifuge, a dewatering screw, a drum thickener, a filter press, and a gravity belt.

12. The method according to claim 1, wherein controlling further comprises
    comparing obtained data and predicted data from the sludge with stored data on a server,
    identifying a set in the stored data which is similar to one of the group of the obtained and predicted data,
    retrieving method operational settings related to the set of stored data, wherein the method operational settings are for operating at least digestion reactor and a dewatering device, and
    applying at least one of the retrieved operation settings to at least digestion reactor and dewatering device.

13. The method according to any of claim 1, wherein controlling comprises adapting at least one of pH, redox potential, volatile fatty acid concentration, alkalinity, cation concentration, and temperature, of at least one digestion reactor and dewatering device.

14. The method according to claim 1,
    wherein obtained data is mathematically weighed, and
    wherein obtained data is mathematically averaged, and
    wherein to be obtained data is mathematically predicted.

15. The method according to any of claim 1, wherein the method is performed according to one of the group of continuously, at regular intervals, after an incident, based on statistical process control, and combinations thereof.

16. The method according to claim 1, wherein dry matter is measured according to one of the group of in parallel to a fluid connection, with a radio wave device, with an optical device, and a combination thereof; and wherein flow is controlled with one of the group of at least one valve, at least one pump, and a combination thereof.

17. The method according to claim 3,
    wherein during dewatering a dry matter content is measured every 0.1-2440 minutes, and
    wherein a dry matter content is used to adapt setting of the dewatering device.

18. The method according to claim 1,
    wherein the pH of at least the first digestion reactor is controlled to maintain above 5.0, and
    wherein the redox value of at least one digestion reactor is controlled to maintain below-200 mV, and
    wherein the pH of at least one digestion reactor is controlled to maintain below 9, and
    wherein the redox value of at least one digestion reactor is controlled to maintain above-450 mV, and
    wherein an amount of foam is controlled by adding 0.01-1 wt. % antifoam, and
    wherein antifoam comprises a component selected from essential oils, fatty acid esters, poly alkyl glycols, alkane hydrocarbons, poly dimethyl siloxane, silicon emulsions, polyethers, silicon polymers, Simethicone, derivatives thereof, and combinations thereof.

19. The method according to claim 1,
    wherein an effluent of the Nth reactor is treated in a stirred tank reactor before dewatering, and
    wherein microbial sludge is one of the group of granulated, is flocculated, forms a biofilm, and a combination thereof, and
    wherein the system is loaded with >1 kg COD, and
    wherein at least one flow is monitored by a power consumption of a pump providing said flow, and
    wherein aqueous sludge is pre-treated prior to step (a)
    wherein >2 kg sludge/m3 is present per reactor.

20. A reactor set-up for serially treating aqueous organic sludge by anaerobic digestion, comprising
    a series of N digestion reactors, wherein N≥2,
    between an nth digestion reactor and an n+1th digestion reactor a fluidic connection,
    a sludge input for the first digestion reactor,
    an effluent output for the Nth digestion reactor,
    a fluidic effluent connection between the second digestion reactor and the first digestion reactor,
    a fluidic effluent connection between the Nth digestion reactor and at least one lower ranked digestion reactor,
    at least one controller for controlling at least one of the group of feeding and removing
        by obtaining at least two values of pH, an amount of dry sludge in the feed, temperature of at least one digestion reactor, type of input sludge, and wherein values are obtained of at least one of the sludge in the input and of at least the first of the N digestion reactors, and
        by regulating a fluid level in at least one digestion reactor to prevent overflow of an nth reactor to a subsequent n+1th reactor and a parameter selected from at least one flow, an amount of sludge in a digestion reactor, an amount of anti-foam in a digestion reactor, and combinations thereof, wherein a flow is selected from feed and removal flows to and from the N digestion reactors, and for controlling dewatering by obtaining values of pH and redox values, wherein values are obtained of at least one of the sludge in the input and of at least the first of the N digestion reactors, and by regulating a flow between at least one Nth digestion reactor and post-digester and dewatering apparatus,
    at least one heater for digesting the organic sludge in at least one digestion reactor at a temperature from 20-70° C. during a period of time of more than 3 days, and
    at least one pump for providing flow.

* * * * *